United States Patent
Steur et al.

(10) Patent No.: US 8,667,634 B2
(45) Date of Patent: Mar. 11, 2014

(54) SYSTEM FOR AXIAL BRISTLE MOTION IN A TEETH CLEANING MOUTHPIECE

(75) Inventors: Jelte Steur, Delft (NL); Martinus Bernardus Stapelbroek, Rolde (NL); Evert Alle Helfrich, Groningen (NL); Arif Veendijk, Assen (NL)

(73) Assignee: Koninklijke Philips N.V., Eindhoven (NL)

( * ) Notice: Subject to any disclaimer, the term of this patent is extended or adjusted under 35 U.S.C. 154(b) by 164 days.

(21) Appl. No.: 13/132,952

(22) PCT Filed: Dec. 4, 2009

(86) PCT No.: PCT/IB2009/055510
§ 371 (c)(1),
(2), (4) Date: Jun. 6, 2011

(87) PCT Pub. No.: WO2010/076692
PCT Pub. Date: Jul. 8, 2010

(65) Prior Publication Data
US 2011/0258792 A1 Oct. 27, 2011

Related U.S. Application Data

(60) Provisional application No. 61/141,071, filed on Dec. 29, 2008.

(51) Int. Cl.
*A46B 13/02* (2006.01)
(52) U.S. Cl.
USPC .................................. 15/22.1; 15/21.1

(58) Field of Classification Search
USPC .................. 15/21.1, 167.1, 167.2, 22
See application file for complete search history.

(56) References Cited

U.S. PATENT DOCUMENTS

| | | | |
|---|---|---|---|
| 3,683,442 A | 8/1972 | Holly | |
| 4,223,417 A | 9/1980 | Solow | |
| 4,224,710 A * | 9/1980 | Solow | 15/22.1 |
| 4,795,347 A * | 1/1989 | Maurer | 15/22.1 |
| 2007/0009856 A1 | 1/2007 | Jones et al. | |

FOREIGN PATENT DOCUMENTS

| | | |
|---|---|---|
| DE | 102005059775 A1 | 6/2007 |
| JP | 01212548 A | 8/1989 |
| JP | 10066704 A | 3/1998 |
| WO | 2008142600 A1 | 11/2008 |

* cited by examiner

*Primary Examiner* — Robert Scruggs

(57) ABSTRACT

The mouthpiece includes a mouthpiece carrier member (14) having upper and lower sections which are adapted to receive the upper and lower teeth of a user. The mouthpiece carrier member has several embodiments which include side members and an intermediate member or members connecting the two side members to define the two sections. A bristle field (20) is mounted on the mouthpiece carrier member for contact with the surfaces of the teeth. The mouthpiece carrier member is moved in such a manner to produce a bristle action which has a significant axial component, resulting in the bristle tufts moving toward the teeth, contacting the teeth and moving away from the teeth, producing cleaning action on the teeth.

3 Claims, 4 Drawing Sheets

SYSTEM FOR AXIAL BRISTLE MOTION IN A TEETH CLEANING MOUTHPIECE This invention relates generally to mouthpieces for cleaning teeth, and more specifically concerns various drive arrangements for the mouthpiece which produce an axial bristle movement toward and away from the teeth to assist in cleaning thereof.

Bristle tuft motion for a toothbrush or in a mouthpiece is recognized to be an important consideration in effective cleaning of teeth. One type of bristle motion which has been shown to be effective is axial motion, in which there is a significant component of bristle motion toward and away from the teeth, often referred to as a tapping or a light hammering motion. In a mouthpiece teeth-cleaning appliance, however, the length of the stroke which is acceptable is quite limited for most of the population because of space limitations. The motion of the bristles should be axial, i.e. close to perpendicular to the teeth. However, use of such a tapping motion in a mouthpiece is complicated by the fact that the bristles will be impacting different teeth from different directions, because of the arrangement (arch) of the teeth relative to the configuration of the mouthpiece. Further, the user's hand typically cannot be regarded as a reference point which the bristles forces can react against. The forces require a new reference, i.e. ground point, or they will tend to cancel.

The disclosure herein is directed toward a number of different embodiments whose bristle motion includes a significant component directed toward and away from the teeth, i.e. a tapping motion against the teeth.

Accordingly, the mouthpiece for cleaning teeth, comprises: a mouthpiece carrier member having upper and lower sections adapted to receive the upper and lower teeth of a user; a bristle tuft assembly mounted on the mouthpiece carrier member; and a system for moving the mouthpiece carrier sections to produce a bristle motion which has a significant axial component, resulting in the bristles moving toward the teeth, contacting the teeth and moving away from the teeth for cleaning thereof.

Figure 1:
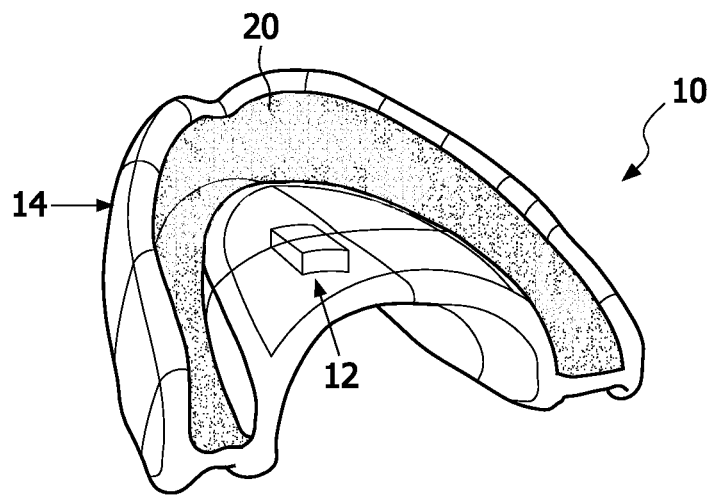
FIG. 1 is a perspective view of a typical dental cleaning mouthpiece for reference to the various embodiments disclosed hereinafter.

FIG. 1 shows a mouthpiece 10 which uses bristles to produce a cleaning action in operation on the teeth of a user. The mouthpiece generally includes a power drive controller unit 12, a mouthpiece carrier assembly arch 14 which includes upper and lower portions generally in a horseshoe configuration which are adapted to receive the upper and lower teeth of a user, respectively. Bristles tufts 20, defining a bristle field or fields, are positioned on the interior surfaces of the upper and lower sections of the carrier assembly 14 to produce the cleaning action.

As indicated above, an axial motion of bristles tufts in the direction of the teeth can produce an effective cleaning action. The following various embodiments produce a motion which includes a significant axial component to accomplish such cleaning.

Figure 2:
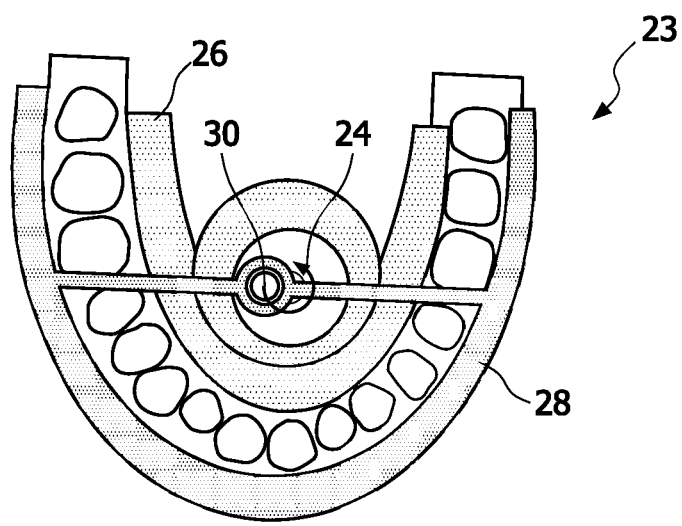
FIG. 2 is a top view of one embodiment of an axial bristle drive system for a mouthpiece.

FIG. 2 shows one embodiment for a mouthpiece 23 that includes a rotary motor 24 which rotates continuously when the mouthpiece is actuated. The drive shaft of the motor 24 is connected to an inner portion 26 of the carrier arch assembly for receiving the teeth, to which bristle tufts are attached. The outer portion 28 of the carrier arch assembly is driven by an eccentric 30 connected to the driveshaft. The resulting motion of the carrier arch assembly and the bristle tufts includes a motion component for the bristle tufts toward and away from the teeth (tapping motion) as well as a sideways sweeping (scrubbing) action.

Figure 3:
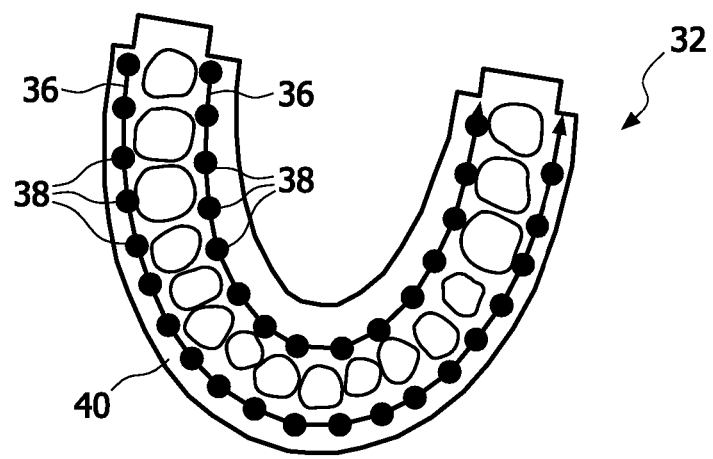
FIG. 3 is a top view of another embodiment of an axial bristle drive system for a mouthpiece.

FIG. 3 shows a mouthpiece 32 which includes a flexible rod or cable element 36 on which are mounted a plurality of balls or cams 38. The cable 36 could alternatively be a leaf spring or other type of flexible rod. The cable is movable linearly by a linear or oscillating motion produced by a motor (not shown). A flexible membrane 40 with bristle tufts (not shown for clarity) is positioned adjacent the teeth and remains stationary in the linear direction (along the teeth). As the balls 38 move over the teeth, back and forth by motor action, the flexible membrane 40 is pushed in and out, toward and away from the teeth. This results in a tapping action of bristle tufts on the membrane against the teeth.

Figure 4:
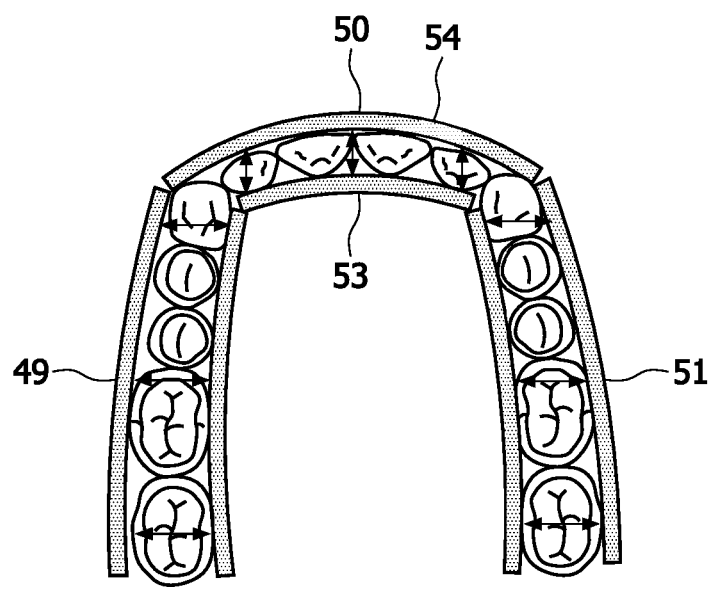
FIG. 4 shows a still further embodiment of an axial bristle drive system.

FIG. 4 shows a portion of a mouthpiece in which the carrier assembly arch is split into three different parts 49, 50 and 51 for coverage of all the teeth for both the upper and lower sections. In this case, two opposing portions, e.g. 53, 54, for each part (e.g. 50) are movable axially back and forth toward each other to contact the teeth. This independent actuation produces a bristle tapping action against the surfaces of the teeth for each part of the carrier assembly arch.

Figure 5:
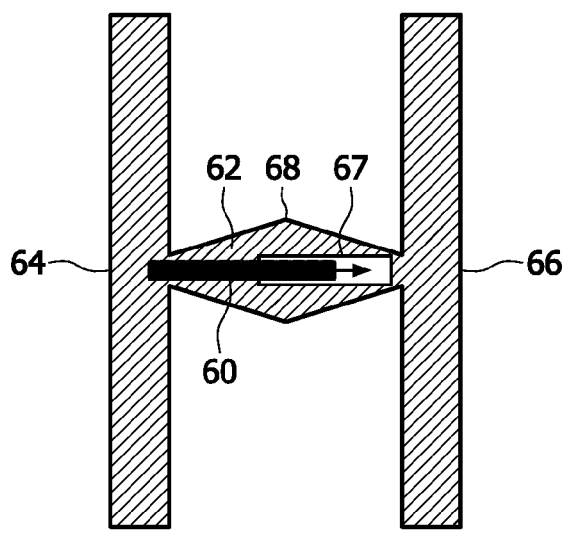
FIG. 5 shows yet another embodiment of an axial bristle drive system.

FIGS. 5-9 show various arrangements for accomplishing the movement of the carrier arch assembly parts. In FIG. 5, a movable cylinder 60 in a housing 67 is positioned in an intermediate member 62 which connects side members 64, 66, which together define the carrier assembly arch to receive the upper and lower teeth. Bristle tufts are provided on all the interior (teeth facing) surfaces of the carrier arch assembly, including the exterior and interior surfaces and the occlusal surfaces. Cylinder 60 moves in and out of its housing 67 as a result of the action of either an electromechanical or pressure driver.

The intermediate member 62 is made from a stretchable material such as silicon or rubber. The mid-portion 68 of intermediate member 62 alternately bulges out and then thins back down as cylinder 60 moves in and out of its housing. The occlusal (horizontal) surfaces of the teeth are thus cleaned by bristle tufts on the intermediate member 62, while the vertical surfaces of the teeth are cleaned by bristle tufts on the interior surfaces of side members 64 and 66.

Figure 6:
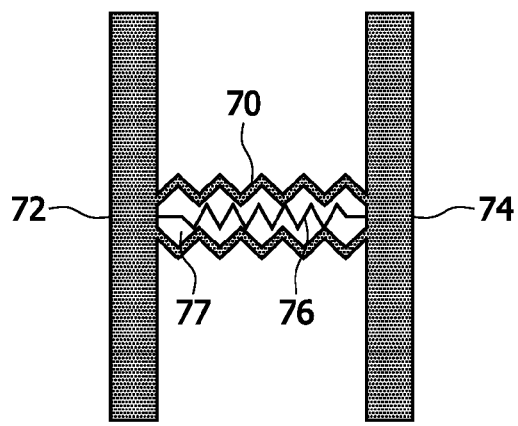
FIG. 6 shows a further embodiment of an axial bristle drive system.

FIG. 6 shows an alternative embodiment, in which a harmonic (sawtooth) shaped intermediate member 70, which connects two side members 72 and 74 of the carrier assembly arch is preloaded with a spring 76. Fluid 77 within the intermediate member is pressurized and depressurized to move (stretch) the harmonic member 70 outwardly and inwardly as well as moving side elements 72 and 74 in and out, providing a bristle tapping action on all surfaces (exterior, interior and occlusal) of the teeth.

Figure 7:
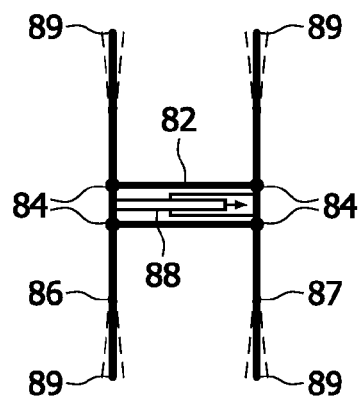
FIG. 7 is a still further embodiment for axial driving motion for a mouthpiece.

In FIG. 7, an intermediate member 82 has hinge points 84 at the opposing ends thereof connected to the side elements 86, 87. A cylinder 88 is driven back and forth, such that the free end tips 89 of the side elements move back and forth, providing a tapping bristle tuft action on the teeth. Cleaning of the occlusal (horizontal) surfaces of the teeth is produced by a chewing motion by the user or alternatively by the expansion of the surfaces of intermediate member 82 when it alternately shortens and lengthens by action of cylinder 88.

Figure 8:
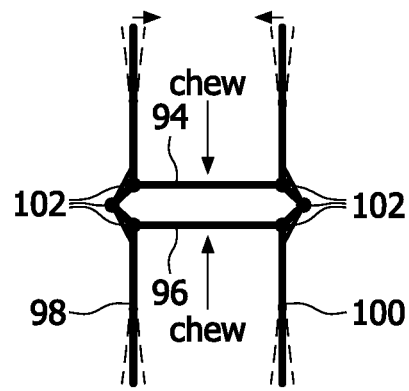
FIGS. 8 and 9 show further embodiments of an axial bristle drive system involving a chewing action of the user.

FIG. 8 shows an embodiment in which a chewing motion on the mouthpiece produces a tapping bristle action. Two intermediate elements/members 94 and 96 are hinged to side elements 98 and 100 at hinge points 102 and are forced together by a chewing motion. Bristle tufts are positioned on the interior surfaces of the side elements and the outer surfaces of intermediate elements 94 and 96. A chewing motion forces the intermediate elements toward each other, such that the tops of the side elements move toward and away from the teeth, producing the tapping action of the bristles on the teeth, resulting in cleaning.

Figure 9:
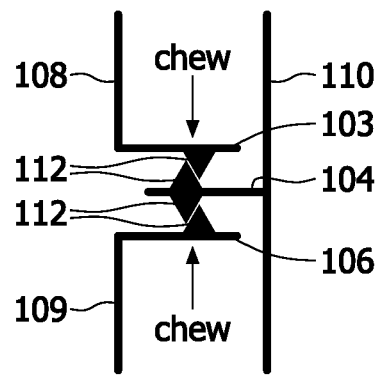

FIG. 9 shows a mouthpiece by which a chewing motion results in forces on horizontal intermediate elements 103, 104, 106. Intermediate elements 103 and 106 are connected to side elements 108 and 109, while intermediate element 104 is connected to side element 110. Triangular shaped members 112 on opposing surfaces of the intermediate elements produce an in-and-out motion of the side elements and a bristle tuft tapping action in response to a chewing action of the user.

Figure 10:
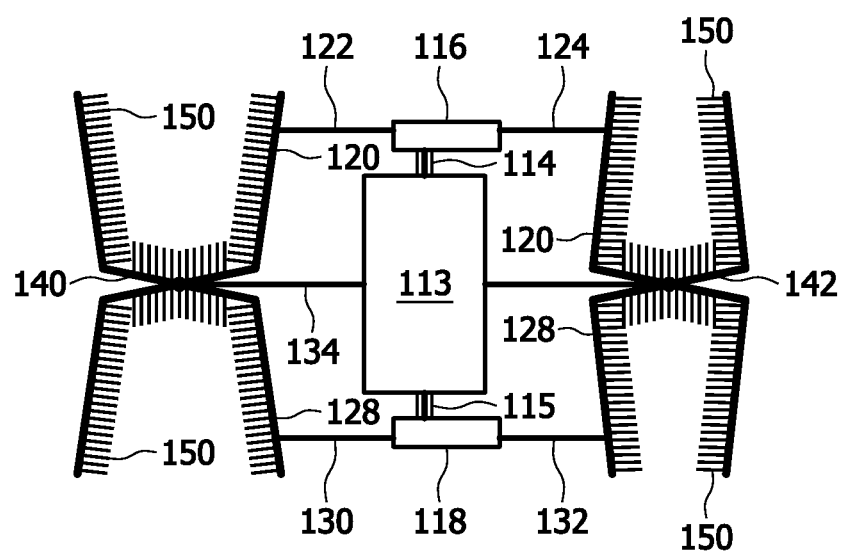
FIG. 10 shows a further embodiment of an axial bristle drive system for a mouthpiece.

FIG. 10 shows a mouthpiece with a motor 113 with two opposing drive shafts 114 and 115 at opposing ends of the motor. Mounted to drive shafts 114, 115 are opposing eccentrics 116, 118. One eccentric 116 is connected to inner side wall 120 of both sides (parts) of the upper section of the dental assembly arch by lines 122, 124, while eccentric 118 is connected to inner side wall 128 of both sides (parts) of the lower section of the dental assembly arch by lines 130, 132. A connection member 134 connects the motor casing to a midpoint between the upper and lower sections of the mouthpiece. As the motor drive shafts turn, the lower right and the upper left portions of the mouthpiece will move either outwardly or inwardly together about fixed points 140, 142. The upper right and lower left portions will move together in the opposite direction. This produces a back-and-forth (axial) motion for the bristle tufts 150 relative to the teeth.

Accordingly, a number of embodiments have been disclosed for producing a bristle movement in a mouthpiece having a significant axial component. Further the drive systems are arranged so that the axial component has a relatively short stroke, on the order of 0.2-3 mm, so that the drive systems can conveniently fit within the mouth.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A mouthpiece for cleaning teeth, comprising:
a mouthpiece carrier member (14) having upper and lower sections adapted to receive the upper and lower teeth of a user;
a bristle tuft assembly (20) mounted on the mouthpiece carrier member; and
a system (12) for moving the mouthpiece carrier sections to produce a bristle motion which has a significant axial component, resulting in bristles in the bristle assembly moving toward the teeth, contacting the teeth and moving away from the teeth for cleaning thereof, wherein the system for moving includes a rotary motor having a rotating drive shaft which is connected to an inner portion (26) of the mouthpiece carrier member and an eccentric (30) mounted on the drive shaft which is connected to an outer portion (28) of the mouthpiece carrier member, wherein action of the motor and the rotating drive shaft produces axial bristle motion as well as a sweeping bristle motion across the teeth.

2. The mouthpiece of claim 1, wherein the moving system is a rotary motor (113) having two drive shafts (114, 115), each of which has an eccentric (116, 118) mounted thereon, including connections (122, 124, 130, 132) between each eccentric and the mouthpiece carrier member, the moving system including a connection (134) which extends between a housing for the motor and a point (140, 142) which connects the upper and carrier sections of the mouthpiece carrier member, wherein action of the motor results in axial motion of the upper and lower sections of the mouthpiece carrier member to produce cleaning action on the teeth.

3. A mouthpiece for cleaning teeth, comprising:
a mouthpiece carrier member having upper and lower sections adapted to receive the upper and lower teeth of the user;
a bristle tuft assembly (20) mounted on the mouthpiece carrier member; and
a system for moving the mouthpiece carrier sections to produce a bristle motion which has a significant axial component, resulting in the bristle tuft assembly moving toward the teeth, contacting the teeth and moving away from the teeth for cleaning thereof, including a pair of elongated, flexible members (36) having a plurality of spaced cam members (38) positioned therealong and a flexible, linearly stationary membrane (40), with bristle tufts attached thereto, positioned between the flexible members and the teeth, wherein linear movement of the flexible members longitudinally along the teeth results in axial movement of the membrane and the bristle tufts moving into contact with and then away from the teeth.

* * * * *